US009724026B2

(12) United States Patent
Wiser et al.

(10) Patent No.: US 9,724,026 B2
(45) Date of Patent: Aug. 8, 2017

(54) PASSIVE DETECTION OF PULSE

(71) Applicant: Verily Life Sciences LLC, Mountain View, CA (US)

(72) Inventors: Robert Francis Wiser, San Francisco, CA (US); Brian Otis, Saratoga, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 253 days.

(21) Appl. No.: 14/473,865

(22) Filed: Aug. 29, 2014

(65) Prior Publication Data

US 2016/0058315 A1    Mar. 3, 2016

(51) Int. Cl.
*A61B 5/1455* (2006.01)
*A61B 5/00* (2006.01)
*A61B 5/024* (2006.01)
*G02B 1/04* (2006.01)

(52) U.S. Cl.
CPC ...... *A61B 5/14555* (2013.01); *A61B 5/02427* (2013.01); *A61B 5/14552* (2013.01); *A61B 5/6821* (2013.01); *A61B 5/0031* (2013.01); *A61B 2560/0214* (2013.01); *G02B 1/043* (2013.01)

(58) Field of Classification Search
CPC . A61B 5/02444; A61B 5/6821; A61B 5/0059; A61B 5/14555; G02C 7/04
See application file for complete search history.

(56) References Cited

U.S. PATENT DOCUMENTS

| 4,485,820 | A  | 12/1984 | Flower |
| 4,846,183 | A  | 7/1989 | Martin |
| 5,190,038 | A  | 3/1993 | Polson et al. |
| 5,954,644 | A  | 9/1999 | Dettling et al. |
| 6,122,536 | A  | 9/2000 | Sun et al. |
| 6,312,393 | B1 | 11/2001 | Abreu |
| 6,347,242 | B1 | 2/2002 | Friedlander |
| 6,731,962 | B1 | 5/2004 | Katarow et al. |

(Continued)

OTHER PUBLICATIONS

International Search Report and Written Opinion of International Application No. PCT/US2015/047155 dated Dec. 14, 2015 (mailed Dec. 14, 2015).

*Primary Examiner* — Eric Winakur
(74) *Attorney, Agent, or Firm* — McDonnell Boehnen Hulbert & Berghoff LLP

(57) ABSTRACT

A body-mountable light sensing device includes a photodiode configured to receive light from a portion of subsurface vasculature and electronics configured to operate the photodiode to measure the received light. The electronics include a photodiode voltage source configured to reverse bias the photodiode, a current mirror, and a sigma-delta modulator configured to generate a digital output related to the received light and having a high resolution while using low power. The digital output could be used to determine a pulse rate or other properties of blood in the portion of subsurface vasculature by detecting absorption of ambient light by blood in the portion of subsurface vasculature. Components of the body-mountable device could be embedded in a polymeric material configured for mounting to a surface of an eye. The digital output and/or related information could be wirelessly communicated by the body-mountable device.

20 Claims, 7 Drawing Sheets

(56) References Cited

U.S. PATENT DOCUMENTS

| | | | |
|---|---|---|---|
| 7,155,133 B2* | 12/2006 | Stewart | H04B 10/6931 |
| | | | 250/214 R |
| 8,764,185 B1 | 7/2014 | Biederman et al. | |
| 2007/0270673 A1 | 11/2007 | Abrams et al. | |
| 2011/0060530 A1 | 3/2011 | Fennell | |
| 2012/0259188 A1 | 10/2012 | Besling | |
| 2013/0041591 A1 | 2/2013 | Lamego | |
| 2013/0112848 A1* | 5/2013 | Lin | G01J 1/44 |
| | | | 250/206 |
| 2014/0081161 A1 | 3/2014 | Kuno | |
| 2014/0143064 A1 | 5/2014 | Tran | |
| 2014/0194708 A1* | 7/2014 | Ho | A61B 5/0004 |
| | | | 600/318 |

* cited by examiner

PASSIVE DETECTION OF PULSE

BACKGROUND

Unless otherwise indicated herein, the materials described in this section are not prior art to the claims in this application and are not admitted to be prior art by inclusion in this section.

Optical properties of blood (e.g., absorptivity at a specified wavelength(s)) can differ from optical properties of surrounding tissue (e.g., skin, the walls of blood vessels); further, optical properties of blood can be related to other properties of the blood (e.g., the oxygen binding state of hemoglobin in the blood). Thus, the presence and/or amount of blood in a tissue, the oxygen saturation of the blood, or other properties of blood and/or tissue can be detected by illuminating the blood and/or tissue and detecting a property of light reflected, refracted, transmitted, scattered, or otherwise emitted by the blood and/or tissue in response to the illumination. A measurement of the volume of blood in a tissue over time (e.g., by measuring the degree to which the tissue and/or blood absorb an illuminating light over time) can be used to determine a pulse rate, a flow profile, a pressure profile, or some other information about perfusion and/or flow of blood in the tissue. A measurement of the amount of illumination that is absorbed by blood at two or more specified wavelengths can allow the determination of an oxygen saturation of the blood.

SUMMARY

Some embodiments of the present disclosure provide a body-mountable device including: (i) a photodiode, wherein the photodiode is configured to detect light received from a portion of subsurface vasculature, wherein the light received from the portion of subsurface vasculature is related to blood in the portion of subsurface vasculature; (ii) a photodiode voltage source, wherein the photodiode voltage source is configured to apply a voltage to the photodiode such that the photodiode is reverse biased, wherein a current through the photodiode is related to the light received from the portion of subsurface vasculature; (iii) a sigma-delta modulator, wherein the sigma-delta modulator is configured to receive an input and to provide a digital output related to the input; and (iv) a current mirror, wherein the current mirror is configured to provide an output current that is related to the current through the photodiode, wherein the input received by the sigma-delta modulator is the output current of the current mirror.

Some embodiments of the present disclosure provide a method including: (i) mounting a body-mountable device to an external body surface proximate to a portion of subsurface vasculature, wherein the body-mountable device includes (A) a photodiode, wherein the photodiode is configured to detect light received from the portion of subsurface vasculature, wherein the light received from the portion of subsurface vasculature is related to blood in the portion of subsurface vasculature, (B) a photodiode voltage source, wherein the photodiode voltage source is configured to apply a voltage to the photodiode such that the photodiode is reverse biased and such that a current through the photodiode is related to the light received from the portion of subsurface vasculature, (C) a sigma-delta modulator, wherein the sigma-delta modulator is configured to receive an input and to provide a digital output related to the input, and (D) a current mirror, wherein the current mirror is configured to provide an output current that is related to the current through the photodiode, wherein the input received by the sigma-delta modulator is the output current of the current mirror; (ii) operating the body-mountable device to generate the digital output; and (iii) determining a property of blood in the portion of subsurface vasculature based on the generated digital output.

These as well as other aspects, advantages, and alternatives, will become apparent to those of ordinary skill in the art by reading the following detailed description, with reference where appropriate to the accompanying drawings.

DETAILED DESCRIPTION

Figure 1:
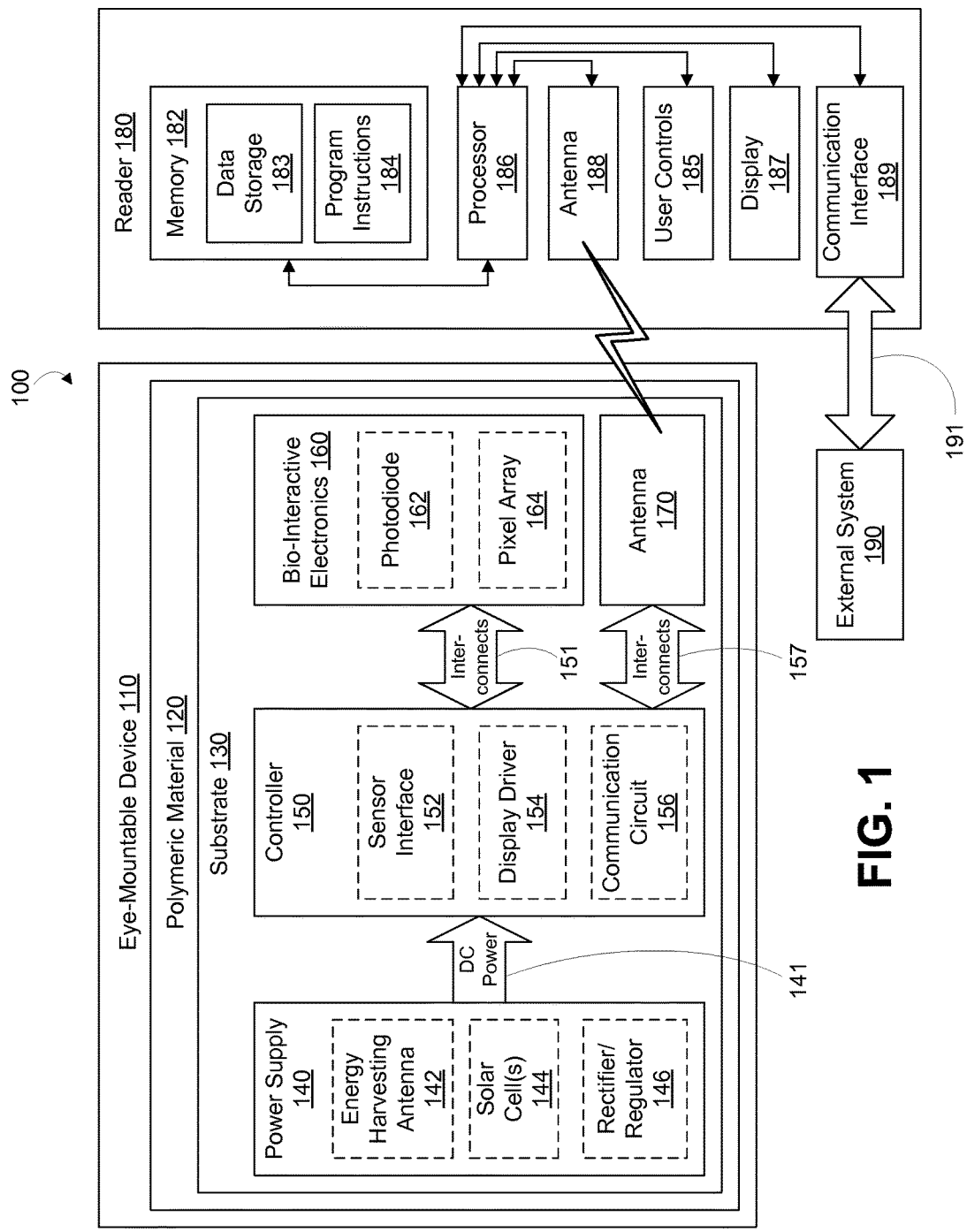
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Embodiments provided herein include a body-mountable device configured to optically detect a property of blood in a portion of subsurface vasculature (e.g., a volume of blood, a content and/or saturation of one or more gasses in the blood) by detecting light (e.g., visible light, infrared light, ultraviolet light) received from the portion of subsurface vasculature (e.g., detecting an intensity, a polarization, a color, a spectral profile of the received light) in response to illumination of the portion of subsurface vasculature by ambient light (e.g., direct or indirect sunlight, light from a lamp or lighting fixture, light from a display, light from some other ambient light in the environment of the portion of subsurface vasculature) and/or by light emitted by a light source in the body-mountable device. Optical detection of the light received from the portion of subsurface vasculature could include reverse-biasing a photodiode configured to receive the light from the portion of subsurface vasculature and using a current-mode sigma-delta modulator to generate a digital output related to a current through the reverse-biased photodiode that is related to a property of the light received by the photodiode. Further, a current mirror could be used to present a current to the sigma-delta modulator that is related to the current through the photodiode.

In some embodiments, the body-mountable device is configured to detect a volume of blood in the portion of subsurface vasculature (e.g., to allow photoplethysomographic application(s)). For example, the body-mountable device could be configured and/or operated to detect light received from the portion of subsurface vasculature that is related to the absorption of ambient light by blood in the portion of subsurface vasculature that is, in turn, related to the volume of blood in the portion of subsurface vasculature. Such volume or other measurements could be performed using the body-mountable device a plurality of times, and a plurality of respectively detected blood volumes or other properties could be used to determine a flow rate, a pulse rate, a flow profile, or some other information about the blood in the portion of subsurface vasculature and/or about a health state of a human to which the body-mountable device is mounted.

In some embodiments, the body-mountable device could include a further photodetector (e.g., another photodiode and sigma-delta modulator, and/or a second photodiode connected to a first sigma-delta modulator that is also connected to the first photodiode) configured to detect another property of light received from the portion of subsurface vasculature and/or from another portion of subsurface vasculature. Such a second photodetector could be used to determine some property of a human to which the body-mountable device is mounted. For example, the photodiode could be configured to detect the intensity of received light within a first range of wavelengths, a further photodetector of the body-mountable device could be configured to detect the intensity of received light within a second range of wavelengths, and an oxygen saturation or other property of a gas content of blood from which the light was received could be determined based on the detected intensities. Additional properties of blood in the portion of subsurface vasculature and/or other applications of a body-mountable device as described herein are anticipated.

Variations in or other properties of light received from a portion of subsurface vasculature in response to illumination of the portion of subsurface vasculature by ambient light could have very small values, and a related current and/or change in current through the photodiode could have a very small amplitude. Thus, the sigma-delta modulator could be configured to have a very high current resolution. For example, the sigma-delta modulator could be configured and/or operated to have a capacitor sink current, a comparator clock frequency, or some other property or combination of properties such that the digital output of the sigma-delta modulator contains information related to the current through the photodiode that has a resolution that is less than approximately 100 picoamps. Further, the photodiode, sigma-delta modulator, and related components (e.g., a feedback amplifier configured to apply a specified voltage to the photodiode, a current mirror configured to apply a current to the sigma-delta modulator that is substantially equal to the current through the photodiode) could be configured to operate using very little power (e.g., less than approximately 500 nanoamps) according to the constraints of an application (e.g., a wearable or otherwise battery-powered application, an application powered by wireless energy, an application powered by ambient energy harvested form the environment of the body-mountable device).

Body-mountable devices as described herein could take a variety of forms and be configured in a variety of ways to be mounted on body locations according to an application. Such devices could include mounts (e.g., straps, adhesives) or other features (e.g., a geometry configured to conform to and/or around an element of human anatomy) configured to position the body-mountable device relative to a portion of subsurface vasculature such that the photodiode can receive light from the portion of subsurface vasculature. The photodiode could receive the received light directly, or through one or more filters, mirrors, lenses, diffraction gratings, and/or other optical elements. Body-mountable devices could be powered by a battery, a tether, or some other method. In some examples, a body-mountable device could be powered by radiated energy received at the body-mountable device. Such received radiated energy could be rectified and/or regulated in real time to power the body-mountable device. For example, power can be generated from incident radio frequency radiation inductively harvested by a suitable antenna of the body-mountable device. Additionally or alternatively, power can be generated from incident light harvested by photovoltaic cells (e.g., solar cells). A rectifier and/or regulator can then output a stable DC voltage to power the body-mountable device. Such an antenna can be arranged as a loop of conductive material that is connected to electronics of the body-mountable device. Furthermore, the body-mountable device can be configured to wirelessly communicate information (e.g., a signal related to a digital output of the sigma-delta modulator) to an external system by modifying the impedance of the antenna so as to characteristically modify RF backscatter from the antenna in a manner that can be detected by the external system.

In some embodiments, the body-mountable device is situated in an eye-mountable device configured to rest on corneal tissue, similar to a contact lens. The body-mountable device includes a photodiode and electronics configured to operate the photodiode (e.g., feedback amplifiers, current mirrors, the sigma-delta modulator) and to perform other functions of the body-mountable device (e.g., to wirelessly indicate a signal related to the output of the sigma-delta modulator, to power the body-mountable device using radio frequency energy received using an antenna) which can be disposed on a substrate embedded in the lens material. The substrate can be embedded near the periphery of the eye-mountable device, such as a ring-shaped substrate embedded in the contact lens material around the circumference, so as to avoid interference with light transmission to the pupil near the central portion of the contact lens. The photodiode can be arranged on the substrate to face inward, toward the surface of the cornea, such that the photodiode can receive light from a portion of subsurface vasculature of the eye (e.g., subsurface vasculature of the sclera). The photodiode may additionally or alternatively be arranged to face outward, away from the surface of the cornea, such that the sensor photodiode can receive light from a portion of subsurface vasculature of an eyelid at least partially covering the eye to which the eye-mountable device is mounted.

The body-mountable device could be operated in a variety of ways relative to the digital output of the sigma-delta modulator. In some embodiments, a controller or other element(s) of the body-mountable device could be configured to determine a property of the blood in the portion of subsurface vasculature (e.g., a volume of blood, an oxygen saturation of blood) based on the digital output of the sigma-delta modulator and/or other elements of the body-mountable device. Additionally or alternatively, the body-mountable device could be configured to indicate (e.g., wirelessly) to an external system a signal related to the digital output of the sigma-delta modulator, and the external system could determine a property of the blood in the portion of subsurface vasculature based on the indicated signal. The digital output of the sigma-delta modulator could be converted (e.g., decimated) to generate a digital value related to the current through the photodiode, and a property of the blood in the subsurface vasculature could be determined based on the generated digital value. Additionally or alternatively, other operations could be performed relative to the digital output of the sigma-delta modulator (e.g., a cross-correlation of the output could be performed to determine a pulse rate of blood in the portion of subsurface vasculature). Conversions, decimation, determinations, or other operations or calculations related to the digital output of the sigma-delta modulator could be performed by the body-mountable device and/or by an external system receiving indicated signals from the body-mountable device related to the digital output of the sigma-delta modulator.

In some examples, an external reader can radiate radio frequency radiation to power the body-mountable device via an energy harvesting system. The external reader may thereby control the operation of the body-mountable device by controlling the supply of power to the body-mountable device. In some examples, the external reader can operate to intermittently interrogate the body-mountable device to provide a reading by radiating sufficient radiation to power the body-mountable device to obtain a measurement and communicate the result. The external reader can also store the sensor results communicated by the body-mountable device. In this way, the external reader can acquire a series of received light measurements or other information related to light received from a portion of subsurface vasculature over time without continuously powering the body-mountable device.

The external reader may be provided as a mobile device with software applications for displaying the sensor results. The external reader may also include a communications interface that can be configured to convey measured and/or determined information to other systems for display, data storage, and/or analysis.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques and/or plating techniques can be employed to pattern materials on the substrate 130. The substrate 130 can be a relatively rigid material, such as polyethylene terephthalate ("PET"), parylene, or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in the center region of the eye-mountable device 110. The bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as a photodiode 162, in bio-interactive electronics 160 to obtain input from the biological environment (e.g., from a portion of subsurface vasculature in the biological environment). Additionally or alternatively, the interaction could involve the use of one or more components, such as pixel array 164, to provide an output to the biological environment.

In one example, the controller 150 includes a sensor interface module 152 that is configured to operate photodiode 162. The photodiode 162 can be operated to generate an output related to light (e.g., visible light, infrared light, ultraviolet light) received from the biological environment. For example, the sensor interface 152 could include a photodiode voltage source configured to apply a specified voltage to the photodiode 162 such that the photodiode 162 is reverse biased and such that a current through the photodiode 162 is related to the light received from the biological environment by the photodiode 162. For example, the current through the photodiode 162 could be related to the intensity of the received light, the intensity of the received light within a specified range of wavelengths, the polarization of the light, or some other property of the received light. The sensor interface 152 could further include a current mirror and a sigma-delta modulator configured such that the current mirror creates an output current related to the current through the photodetector 162 and presents the output current to the sigma-delta modulator. The sigma-delta modulator could be configured to produce a digital output that is related to the output current. The digital output could be used for a variety of applications. Additionally or alternatively, one or more electronic elements or systems configured to operate the photodiode 162 could be disposed as part of the bio-interactive electronics 160 (e.g., by being formed from the same integrated circuit or semiconductor wafer as the photodiode 162) or as part of some other aspect of the eye-mountable device 110.

The light received by the photodiode 162 could be received from the biological environment in response to illumination. The illumination could be illumination from ambient light sources (e.g., the sun, a lamp, some other artificial light source, light reflected off of objects toward the biological environment). The photodiode 162 could be configured to receive light from a particular angle or location relative to the biological environment. For example, the photodiode 162 could be configured to receive light from a portion of subsurface vasculature of an eye by being disposed on and/or configured to receive light through a concave surface of the eye-mountable device 110 (i.e., by being directed toward the concave surface). In some examples, the eye-mountable device 110 could be configured (e.g., weighted, formed with a specified shape) such that the photodiode 162 received light from subsurface vasculature disposed in a lateral region of an eye relative to a pupil of the eye. Additionally or alternatively, the photodiode 162 could be configured to receive light from a portion of subsurface vasculature of an eyelid of an eye when mounted to the eye, by being disposed on and/or configured to receive light through a convex surface of the eye-mountable device 110 (i.e., by being directed toward the convex surface). The eye-mountable device 110 could include multiple photodiodes configured to detect light from multiple portions of a biological environment (e.g., multiple portions of subsurface vasculature of an eye/eyelid) and/or from other sources (e.g., to detect a level of ambient light in the environment of the eye-mountable device 110). The eye-mountable device 110 could include filters, mirrors, lenses, diffraction gratings, or other optical elements configured to focus, block, or otherwise modify light from the biological environment that is received by the photodiode 162.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivably by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or group of more than one antenna) to send and receive wireless signals 171 to and from the eye-mountable device 110. The external reader 180 also includes a computing system with a processor 186 in communication with a memory 182. The external reader 180 can also include one or more of user controls 185, a display 187, and a communication interface 189. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., related to the photodiode 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to perform any of the function described herein. For example, program instructions 184 may cause the external reader 180 to provide a user interface that allows for retrieving information communicated from the eye-mountable device 110 (e.g., sensor outputs or other information related to the photodiode 162) by displaying that information on the display 187 in response to commands input through the user controls 185. The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can also be configured include a communication interface 189 to communicate signals via a communication medium 191 to and from a remote system 190. For example, the remote system 190 may be a smart phone, tablet computer, laptop computer, or personal computer, and communication interface 189 and communication medium 191 may be a Bluetooth module and wireless Bluetooth communication signals, respectively. In this example, the external reader 180 may be configured to send ion concentration data collected by the biosensor 160 to the smart phone, tablet computer, laptop computer, or personal computer for storage and offline analysis. In another example, the remote system 190 is a server at a clinic or physician's office, the communication interface 189 is a WiFi radio module, and the communication medium 191 is elements of the internet sufficient to enable the transfer of data between the remote server and the WiFi radio module. A physician may use this data to make determinations or diagnoses related to the subject's condition. Further, the external reader 180 may be configured to receive signals from a remote server, such as instructions sent by a physician at a remote location to, for example, increase or decrease sampling frequency. Communication interface 189 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The external reader 180 can be a smart phone, digital assistant, or other portable computing device with wireless connectivity sufficient to provide the wireless communication link 171. The external reader 180 can also be implemented as an antenna module that can be plugged into a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earring, etc. or integrated in an article of clothing worn near the head, such as a hat, headband, etc. The external reader 180 could also be implemented in eye glasses or a head-mounted display.

In an example where the eye-mountable device 110 includes a photodiode 162 and related electronics as described herein, the system 100 can be operated to measure one or more properties of a biological tissue (e.g., of blood within or other aspects of a portions of subsurface vasculature) by receiving light (e.g., visible light, infrared light, ultraviolet light) from the biological tissue. For example, light received from a portion of subsurface vasculature could be related to (e.g., could have an intensity related to) a volume of blood in the portion of subsurface vasculature (e.g., by being related to a degree of absorption of ambient light by the blood). One or more properties of the received light detected and/or determined using the photodiode 162 and related electronics could be used to determine a volume of blood in the portion of subsurface vasculature and/or other information related to such. For example, the intensity of the received light could be determined a plurality of times during a plurality of periods of time, and a pulse rate, a blood flow rate, a blood pressure, a blood flow rate and/or pressure profile, or some other information about the blood in the portion of subsurface vasculature could be determined based on the plurality of determined intensities of the received light.

In another example, the eye-mountable device 110 includes a photodiode 162 and related electronics as described herein. The eye-mountable device 110 further includes a photodetector. The photodetector could include a photodiode and related electronics configured similarly to the photodiode 162 and related electronics, could share one or more components (e.g., a common sigma-delta modulator) with the photodiode 162 and related electronics, or could be configured in some other way. Further, the photodiode 162 and photodetector are configured to detect an intensity of light received from a portion of subsurface vasculature within respective first and second ranges of wavelengths. An oxygen saturation of blood in the portion of subsurface vasculature could be determined based on the intensities detected by the photodiode 162 and the photodetector. Other properties of a biological environment could be detected and/or determined using the eye-mountable device 110 (e.g., using the photodiode 162 and related electronics and/or other components of the eye-mountable device 110).

To perform a reading with the system 100 configured as a light sensor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus powers the electronic components within the eye-mountable device 110. Once powered, the controller 150 operates the photodiode 162 to measure one or more properties of light received from a biological environment at one or more points in time. For example, the sensor interface module 152 can generate a digital output (e.g., using a sigma-delta modulator and other electronics of the sensor interface module) related to the light received by the photodiode 162 (e.g., to an intensity of the received light and/or to an intensity of the received light within one or more specified ranges of wavelengths). The measured property or properties can provide the sensor reading ("result") indicative of one or more properties of the biological environment (e.g., an absolute or relative volume of blood within a portion of subsurface vasculature at one or more points in time, an extinction coefficient of the blood in a first range of wavelengths relative to an extinction coefficient of the blood in a second range of wavelengths).

The controller 150 can operate the antenna 170 to communicate the sensor reading back to the external reader 180 (e.g., via the communication circuit 156). Additionally or alternatively, the controller 150 can operate the antenna 170 to communicate other information. For example, the controller 150 could be configured to determine one or more properties of the biological environment based on one or more sensor readings (e.g., could determine an oxygen saturation of blood based on relative intensities of light received from the blood within respective ranges wavelengths) and to subsequently communicate the determined one or more properties back to the external reader 180 using the antenna 170. In another example, the digital output of the sigma-delta modulator (i.e., a series of digital pulses having respective durations during respective periods of time) could be indicated or otherwise communicated to the external reader 180 using the antenna 170. The sensor reading or other information can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a light measurement and communicate the results. For example, the supplied radio frequency radiation can provide sufficient power to measure the light received from the biological environment by the photodiode 162 and modulate the antenna impedance to adjust the backscatter radiation in a manner indicative of the measured light. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of light or other measurements and/or related determined properties (e.g., blood volumes, blood oxygen saturations, pulse rates) over time without continuously powering the eye-mountable device 110.

In other embodiments, the system 100 can operate continuously and supply energy to the eye-mountable device 110 to power the controller 150 and electronics 160 at all times. In some instances, it may be desirable to continuously measure light received from a biological environment in response to illumination (e.g., ambient illumination) and/or to perform some determination related to such a measurement and to collect, store, and or transmit this data.

Figure 2A:
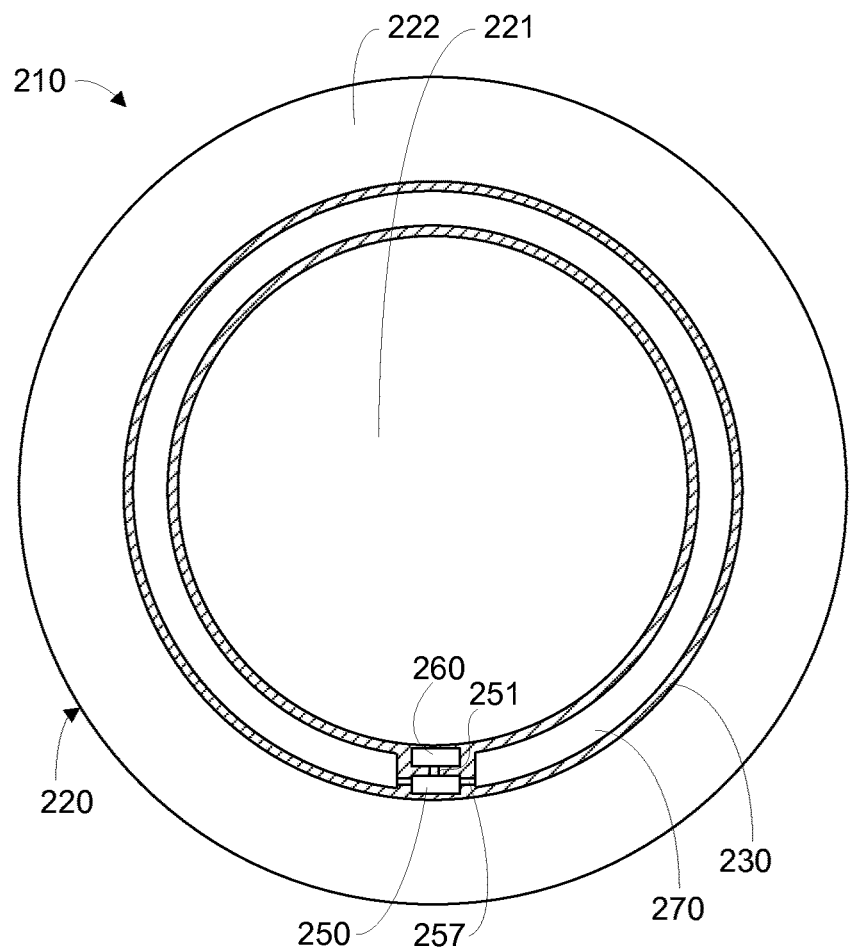
FIG. 2A is a bottom view of an example eye-mountable device.
Figure 2B:
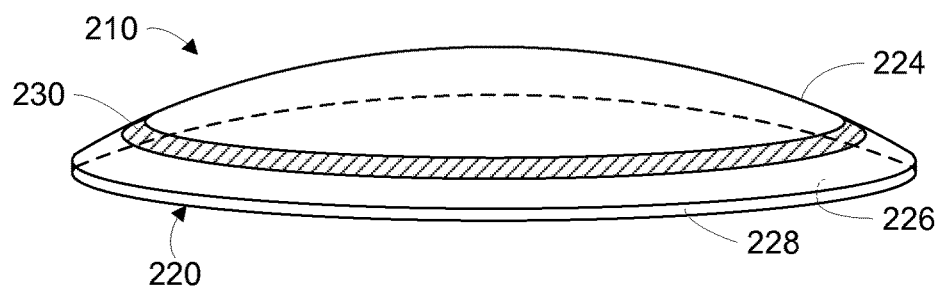
FIG. 2B is an aspect view of the example eye-mountable device shown in FIG. 2A.

FIG. 2A is a bottom view of an example eye-mountable electronic device 210. FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 220 can be formed with one side having a concave surface 226 suitable to fit over a corneal surface of an eye. The opposing side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved out of the page, whereas the center region 221, near the center of the disk is curved in to the page.

A substrate 230 is embedded in the polymeric material 220. The substrate 230 can be embedded to be situated along the outer periphery 222 of the polymeric material 220, away from the center region 221. The substrate 230 does not interfere with vision because it is too close to the eye to be in focus and is positioned away from the center region 221 where incident light is transmitted to the eye-sensing portions of the eye. Moreover, the substrate 230 can be formed of a transparent material to further mitigate any effects on visual perception.

The substrate 230 can be shaped as a flat, circular ring (e.g., a disk with a central hole). The flat surface of the substrate 230 (e.g., along the radial width) is a platform for mounting electronics such as chips (e.g., via flip-chip mounting) and for patterning conductive materials (e.g., via deposition techniques) to form electrodes, antenna(e), and/or connections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical ion sensor, etc.) can be formed from conductive materials patterned on the substrate 230 by a process for precisely patterning such materials, such as deposition, lithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the concave surface 226 of the eye-mountable device 210, the bio-interactive electronics module 260 is mounted to a side of the substrate 230 facing the concave surface 226. Where the bio-interactive electronics module 260 includes a light sensor (e.g., a photodiode), for example, mounting such a sensor on the substrate 230 to be close to the concave surface 226 allows the sensor to sense light (e.g., visible light, infrared light, ultraviolet light) received from portions of subsurface vasculature or other tissues near the surface of the eye. However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made via conductive materials passing through the substrate 230.

The loop antenna 270 can be a layer of conductive material patterned along the flat surface of the substrate to form a flat conductive ring. In some instances, the loop antenna 270 can be formed without making a complete loop. For instance, the antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can be passed through the substrate 230 to the controller 250.

Figure 2D:
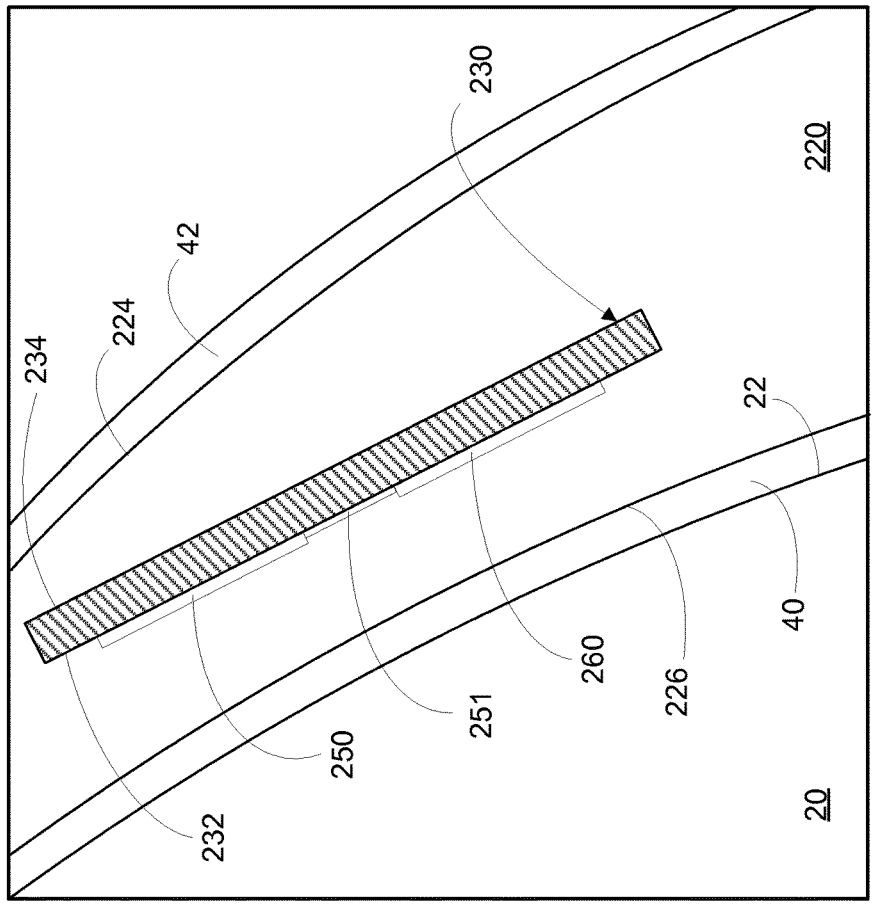
FIG. 2D is a side cross-section view enhanced to show the tear film layers surrounding the surfaces of the example eye-mountable device when mounted as shown in FIG. 2C.
Figure 2C:
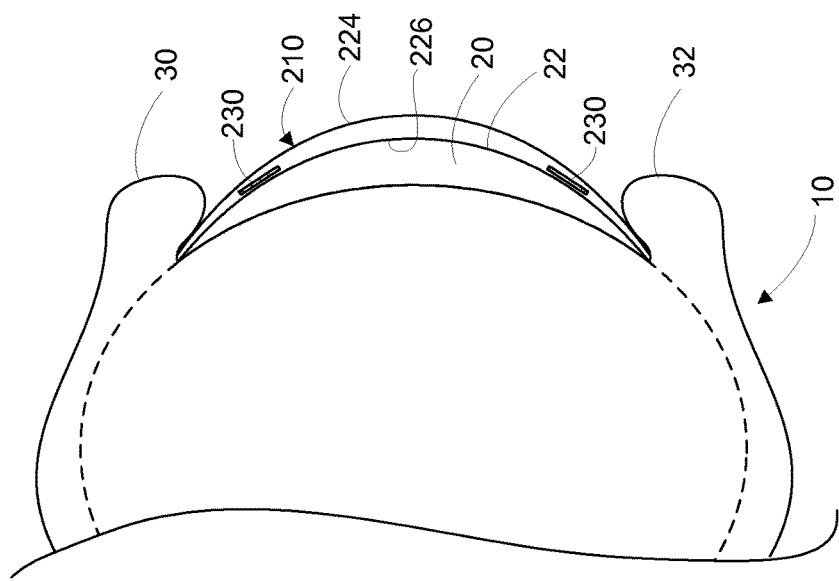
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the concave surface 226. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the inward-facing surface 232 such that the bio-interactive electronics 260 are relatively closer in proximity to the inner tear film layer 42 and the cornea 20 and/or other elements of the eye (e.g., sclera, iris, portions of subsurface vasculature thereof) than if they were mounted on the outward-facing surface 234. With this arrangement, the bio-interactive electronics 260 can receive light from elements of the eye (e.g., cornea 20, sclera, iris, portions of subsurface vasculature thereof) through the concave surface 226. However, in other examples, the bio-interactive electronics 260 may be mounted on the outward-facing surface 234 of the substrate 230 such that the bio-interactive electronics 260 are facing the convex surface 224 and able to receive light from an environment away from the eye 10 (e.g., from an ambient or other light source in the environment of the eye 10, from a portion of subsurface vasculature of an eyelid 30, 32 when said eyelid is wholly or partially covering the bio-interactive electronics of the eye-mountable device 210.

Figure 2E:
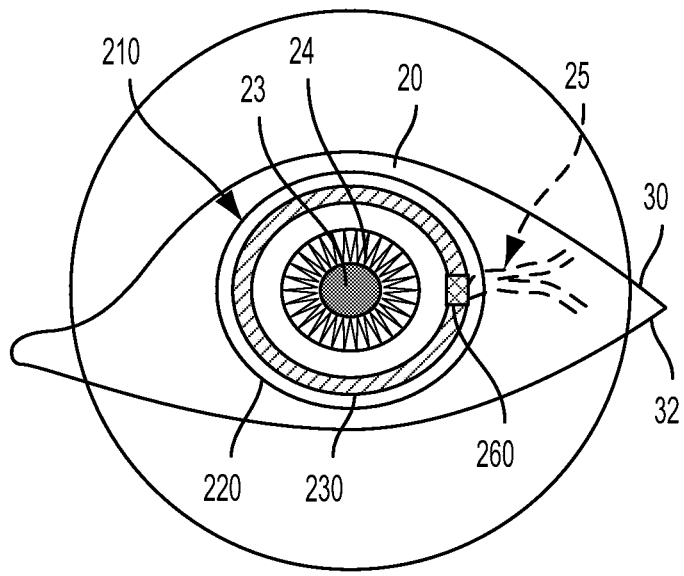
FIG. 2E is a front view of the example eye-mountable device shown in FIGS. 2C and 2D while mounted to a corneal surface of an eye.

The bio-active electronics 260 include a photodiode and related electronics configured to operate the photodiode. FIG. 2E illustrates a front view (i.e., a view from in front of the eye 10) of the eye-mountable device 210 when it is mounted to the eye 10. The photodiode of the bio-active electronics 260 is directed toward the concave surface 226 such that the photodiode receives light from a first portion of subsurface vasculature 25 disposed in a lateral region of the eye 10 relative to the pupil 23 of the eye 10 (e.g., beneath and/or within the sclera of the eye 10).

The photodiode and other elements of the bio-active electronics 260 can be operated and/or configured to generate an output related to light received from the first portion of subsurface vasculature 25. For example, the bio-active electronics 260 and/or the controller 250 (not shown in FIG. 2E) could include a photodiode voltage source configured to apply a specified voltage to the photodiode such that the photodiode is reverse biased and such that a current through the photodiode is related to the light received from the first portion of subsurface vasculature 25 by the photodiode. For example, the current through the photodiode could be related to the intensity of the received light, the intensity of the received light within a specified range of wavelengths, the polarization of the light, or some other property of the received light. The bio-active electronics 260 and/or the controller 250 could further include a current mirror and a sigma-delta modulator configured such that the current mirror creates an output current related to the current through the photodetector and presents the output current to the sigma-delta modulator. The sigma-delta modulator could be configured to produce a digital output that is related to the output current. The digital output could be used for a variety of applications.

Figure 2F:
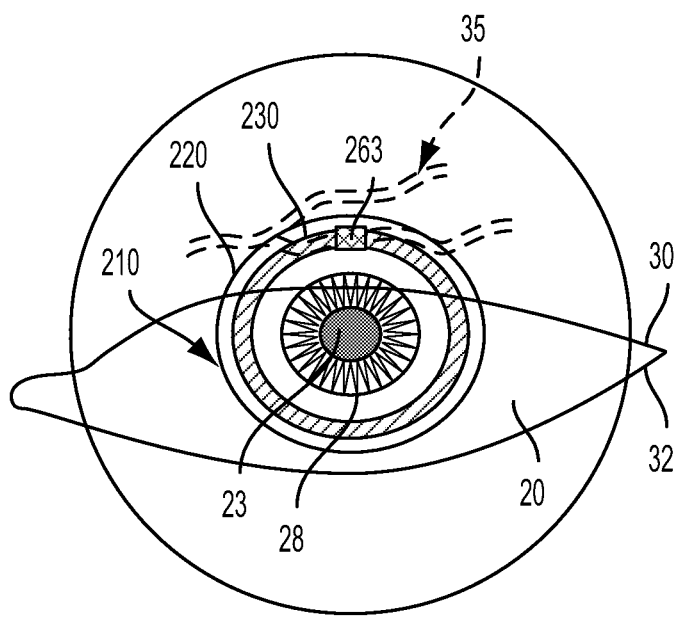
FIG. 2F is a front view of the example eye-mountable device shown in FIGS. 2C and 2D while mounted to a corneal surface of an eye.

The eye-mountable device could include additional or alternative photodiodes and/or other elements of bio-active electronics disposed in different locations relative to the eye-mountable device 210 and/or elements of the eye 10 and directed in different directions such that the additional or alternative photodiodes receive light from other tissues of the eye and/or from the environment of the eye. FIG. 2F illustrates a front view (i.e., a view from in front of the eye 10) of the eye-mountable device 210 when it is mounted to the eye 10 and the upper eyelid 30 is lowered partially over the eye-mountable device 210. FIG. 2F illustrates additional bio-active electronics 263 configured similarly to the bio-active electronics 260 (i.e., including a photodiode and related electronics configured to operate the photodiode to receive light from an environment). The photodiode of the additional bio-active electronics 263 is directed toward the convex surface 224 such that the photodiode receives light from a second portion of subsurface vasculature 35 disposed in the upper eyelid 30 of the eye 10.

Related electronics configured to operate the photodiode of the additional bio-active electronics 263 could be disposed in one or both of the controller 250 (not shown in FIG. 2F) and the additional bio-active electronics 263 and could be configured similarly to the electronics described elsewhere herein regarding operation of a photodiode to detect light received from an environment. Further, one or more components or subsystems (e.g., a sigma-delta modulator) could be shared between the bio-active electronics 260 and the additional bio-active electronics 263 (e.g., by including electronic switches configured to multiplex the input of the sigma-delta modulator from the current mirrors and/or photodiode voltage sources corresponding to the photodiodes of the bio-active electronics 260 and the additional bio-active electronics 263).

Note that the locations of the first 25 and second 35 portions of subsurface vasculature and corresponding locations of the bio-active electronics 260 and the additional bio-active electronics 263 relative to the eye-mountable device 210, the eye 10, and/or the portions of subsurface vasculature 25, 35 are intended as non-limiting, illustrative examples. Bio-active electronics, photodiodes, or other elements of such an eye-mountable device could have different locations than those illustrated. Further, the location of an element of an eye-mountable device (e.g., of the bio-active electronics 260) relative to elements of the eye 10, eyelids 30, 32, portions of subsurface vasculature 25, 35 or other elements could be controlled by a number of methods. For example, the eye-mountable device 210 could be weighted such that the orientation of the eye-mountable device 210 relative to the direction of gravity (and by extension, relative to elements of the eye 10) is controlled. Additionally or alternatively, the eye-mountable device 210 could formed or shaped relative to a shape of the cornea 20, sclera, eyelids 30, 32, or other elements of the eye such that the orientation of the eye-mountable device 210 relative to such elements of the eye 10 is controlled. For example, a lower edge of the polymeric material 220 could be flattened, such that movement of the lower eyelid 32 against the flat lower edge of the polymeric material 220 could act to orient the eye-mountable device 210 relative to the lower eyelid 32.

In some examples, the eye-mountable device 210 could include a plurality of photodiodes arranged on or within the eye-mountable device 210 according to an application. For example, a plurality of photodiodes could be arranged in a curved linear array wholly or partially encircling the central region of the eye-mountable device 210. Photodiodes of such an array could be operated as described herein (e.g., by photodiode voltage sources, current mirrors, and sigma-delta modulators) to detect light received from respective portions of subsurface vasculature of the eye or from some other environment to allow some application as described herein (e.g., detection of blood flow, pulse rate, blood oxygen saturation). In such examples, the plurality of photodiodes could be operated to determine the location of a target portion of vasculature. An individual photodiode of the array that is proximate to the target portion of subsurface vasculature could then be used to determine one or more properties of the portion of vasculature (e.g., blood flow, pulse rate) as described herein. Such a plurality of photodiodes (e.g., a curved linear array of photodiodes) could be operated to allow additional applications; for example, a pattern of vasculature or other property of an eye and/or eyelid could be detected and used, e.g., to identify a wearer of the eye-mountable device 210.

Moreover, it is particularly noted that while the body-mountable light sensor platform described herein by way of example as an eye-mountable device or an ophthalmic device, it is noted that the disclosed light sensing photodiodes and related low-power electronics (e.g., current mirror, photodiode voltage source, sigma-delta modulator) can be applied in other contexts as well. For example, light sensors disclosed herein may be included in wearable (e.g., body-mountable) and/or implantable light sensors. In some contexts, photodiode and related electronics is situated to be substantially encapsulated by bio-compatible polymeric material suitable for being in contact with an external body surface and/or for being implanted such that light can be received from a portion of subsurface vasculature related, e.g., to the volume of blood in the portion of subsurface vasculature. In one example, a mouth-mountable device includes a photodiode and related electronics and is configured to be mounted within an oral environment, such as adjacent a tooth or adhered to an inner mouth surface. In another example, an implantable medical device that includes a photodiode and related electronics may be encapsulated in biocompatible material and implanted within a host organism. Such body-mounted and/or implanted light sensors can include circuitry configured to operate a photodiode and related electronics by providing power to the electronics, by decimating or performing some other operation on an output of the electronics, or some other function(s). The light sensor can also include an energy harvesting system and a communication system for wirelessly indicating the sensor results (i.e., received light).

In other examples, light sensors disclosed herein may be included in wireless light sensors which are not used to measure light received from a portion of subsurface or other vasculature in a human body. For example, light sensors (i.e., photodiodes and related electronics) disclosed herein may be included in body-mountable and/or implantable light sensors used to measure light received from a portion of subsurface or other vasculature of an animal. In another example, light sensors disclosed herein may be included in devices to measure light received from a portion of some other environment in response to illumination (e.g., by one or more ambient light sources), such as a fluid or other element(s) of a river, lake, marsh, forest, prairie, reservoir, water supply, sanitary sewer system, or storm sewer system. For example, light sensors disclosed herein could be included in a low-power environmental sensor that is part of a distributed sensor network. Other applications for photodiodes and related electronics as described herein (e.g., to perform a high-resolution, low-power measurement of light received from a target environment) are anticipated.

III. A Body-Mountable Light Sensor

Figure 3:
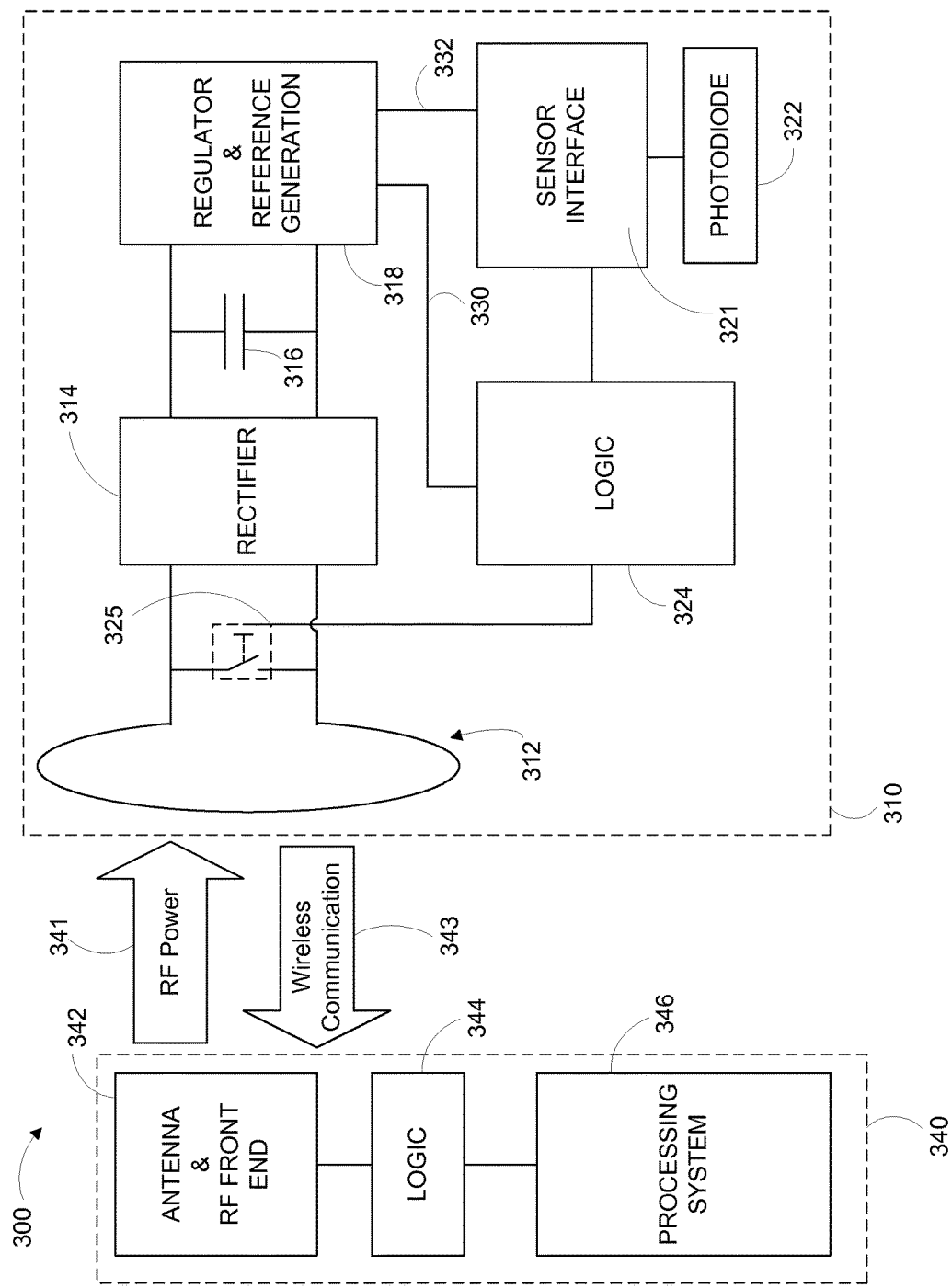
FIG. 3 is a functional block diagram of an example system for detecting light from a portion of subsurface vasculature.

FIG. 3 is a functional block diagram of a system 300 for measuring light (e.g., visible light, infrared light, ultraviolet light) received from a biological environment (e.g., from a portion of subsurface vasculature, e.g., of a sclera or eyelid of an eye). The system 300 includes a body-mountable device 310 with embedded electronic components powered by an external reader 340. The body-mountable device 310 includes an antenna 312 for capturing radio frequency radiation 341 from the external reader 340. The body-mountable device 310 includes a rectifier 314, an energy storage element 316, and a regulator 318 for generating power supply voltages 330, 332 to operate the embedded electronics. The body-mountable device 310 includes a photodiode 322 operated by a sensor interface 321. The body-mountable device 310 includes hardware logic 324 for communicating outputs and/or information derived therefrom from the sensor interface 321 to the external reader 340 by modulating (by means of modulation electronics and interconnects 325) the impedance of the antenna 312. Similar to the eye-mountable devices 110, 210 discussed above in connection with FIGS. 1 and 2A-2F, the body-mountable device 310 can include a mounting substrate embedded within a polymeric material configured to be mounted to an eye. The photodiode 322 can be situated on a mounting surface of such a substrate proximate to the surface of the eye (e.g., corresponding to the bio-interactive electronics 260 on the inward-facing side 232 of the substrate 230) to measure light received from tissues of the eye (e.g., cornea 20, sclera, iris, and/or portions of subsurface vasculature thereof). Alternatively, the photodiode 322 can be situated on a mounting surface of such a substrate distal to the surface of the eye (e.g., on the outward-facing side 234 of the substrate 230) to measure light received from tissues of the eyelid (e.g., portions of subsurface vasculature of the eyelid) and/or from an environment of the eye.

The sensor interface 321 is configured to operate the photodiode 322 to generate an output related to light received from the biological environment. For example, the sensor interface 321 could include a photodiode voltage source configured to apply a specified voltage to the photodiode 322 such that the photodiode 322 is reverse biased and such that a current through the photodiode 322 is related to the light received from the biological environment by the photodiode 322. For example, the current through the photodiode 322 could be related to the intensity of the received light, the intensity of the received light within a specified range of wavelengths, the polarization of the light, or some other property of the received light. The sensor interface 321 could further include a current mirror and a sigma-delta modulator configured such that the current mirror creates an output current related to the current through the photodetector 322 and presents the output current to the sigma-delta modulator. The sigma-delta modulator could be configured to produce a digital output that is related to the output current. The digital output could be used for a variety of applications.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage element 316 (e.g., capacitor) is connected across the output of the rectifier 314 to filter high frequency noise on the DC voltage. The regulator 318 receives the filtered DC voltage and outputs both a digital supply voltage 330 to operate the hardware logic 324 and an analog supply voltage 332 to operate the sensor interface 321 and photodiode 322. For example, the analog supply voltage can be a voltage used by the sensor interface 321 to reverse bias the photodetector 322 and to generate a digital output related to light received by the photodiode 322. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor interface 321 and hardware logic 324. While powered, the sensor interface 321 and hardware logic 324 are configured to measure light received by the photodiode 322 and communicate the results.

The sensor results (i.e., an output of the sensor interface 321 and/or other signals or information derived therefrom) can be communicated back to the external reader 340 via backscatter radiation 343 from the antenna 312. The hardware logic 324 receives the digital output from the sensor interface 321 and modulates (325) the impedance of the antenna 312 in accordance with the digital output that is related to the light received by the photodiode 322. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating patterns over time (e.g., pulse durations and timings) and/or levels of impedance of the antenna 312 with properties of the light received by the photodiode 322). The processing system 346 can then store the indicated sensor results (e.g., received light intensities within one or more ranges of wavelengths, blood volumes, blood flow rates, pulse rates, blood oxygenation, timings of heart beats) in a local memory and/or a network-connected memory. Alternatively, the sensor results can be communicated back to the external reader 340 via an internally generated radio frequency signal 343 from the antenna 312.

In some embodiments, one or more of the features shown as separate functional blocks can be implemented ("packaged") on a single chip. For example, the body-mountable device 310 can be implemented with the rectifier 314, energy storage 316, voltage regulator 318, sensor interface 321, photodiode 322, and/or the hardware logic 324 packaged together in a single chip or controller module. Such a controller can have interconnects ("leads") connected to the loop antenna 312 and/or other components (e.g., the photodiode 322 in such case wherein the photodiode 322 is a separate component form the controller). Such a controller operates to harvest energy received at the loop antenna 312, measure light received by the photodiode 322 using the sensor interface 321, and indicate a signal related to the received light via the antenna 312 (e.g., through backscatter radiation 343).

The sensor interface 321 or other electronics related the operation of a photodetector to receive light from an environment of interest could be configured in a variety of ways. In some applications, a very low-power circuit could be required to optically detect one or more properties of blood in a portion of subsurface vasculature; for example, to detect a volume or change of volume of blood, an absorption coefficient of the blood in one or more ranges of wavelengths, or some other optical properties of the blood and/or portion of vasculature. Such a detection could be performed using very low power by relying on the receiving light emitted from a portion of subsurface vasculature in response to illumination of the portion of subsurface vasculature by, e.g., ambient light. In such an example detection, a level and/or change in level of a property of the received light (e.g., a change in amplitude of the received light) could be very small, such that determination of one or more properties of the portion of subsurface vasculature (e.g., a volume of blood therein) could include measuring the property of the received light at a high resolution.

Such applications could be enabled by the use of electronics as described herein to operate one or more photodiodes to receive light from a portion of subsurface vasculature (or from some other environment of interest) and to generate a digital output related to one or more properties of the received light. That is, such electronics could include a photodiode voltage source configured to reverse bias a photodiode such that a current through the photodiode is related to the received light, a current mirror configured to output a current related to a current through the reverse-biased photodiode, and a sigma-delta modulator configured to receive the output current of the current mirror and to generate a digital output related to the output current of the current mirror. Such elements could be configured in a variety of ways.

Further, electronics configured to operate a photodiode as described herein could include additional elements according to an application. In some examples, a current-mode digital-to-analog convertor (DAC) could be included to sink and/or source a current to the photodiode such that the current received by the current mirror is the photodiode current adjusted by an amount related to the current sunk and/or sourced by the DAC. For example, such a DAC could be operated to remove a baseline level of current through the photodiode that is related to a DC level of the light received from a portion of subsurface vasculature, such that the current presented to the current mirror is related to a time-varying aspect of the light received by the photodiode. A sigma-delta modulator or other elements of the electronics could be used in common between multiple photodiodes (and related electronics, e.g., multiple corresponding photodiode voltage sources and/or current mirrors), e.g., by interposing a multiplexer or other electronic switching components between the sigma-delta modulator and the multiple photodiodes and related electronics. Other operations and applications of such a DAC, or of other additional or alternative elements of electronics configured to operate a photodiode as described herein, are anticipated.

Figure 4:
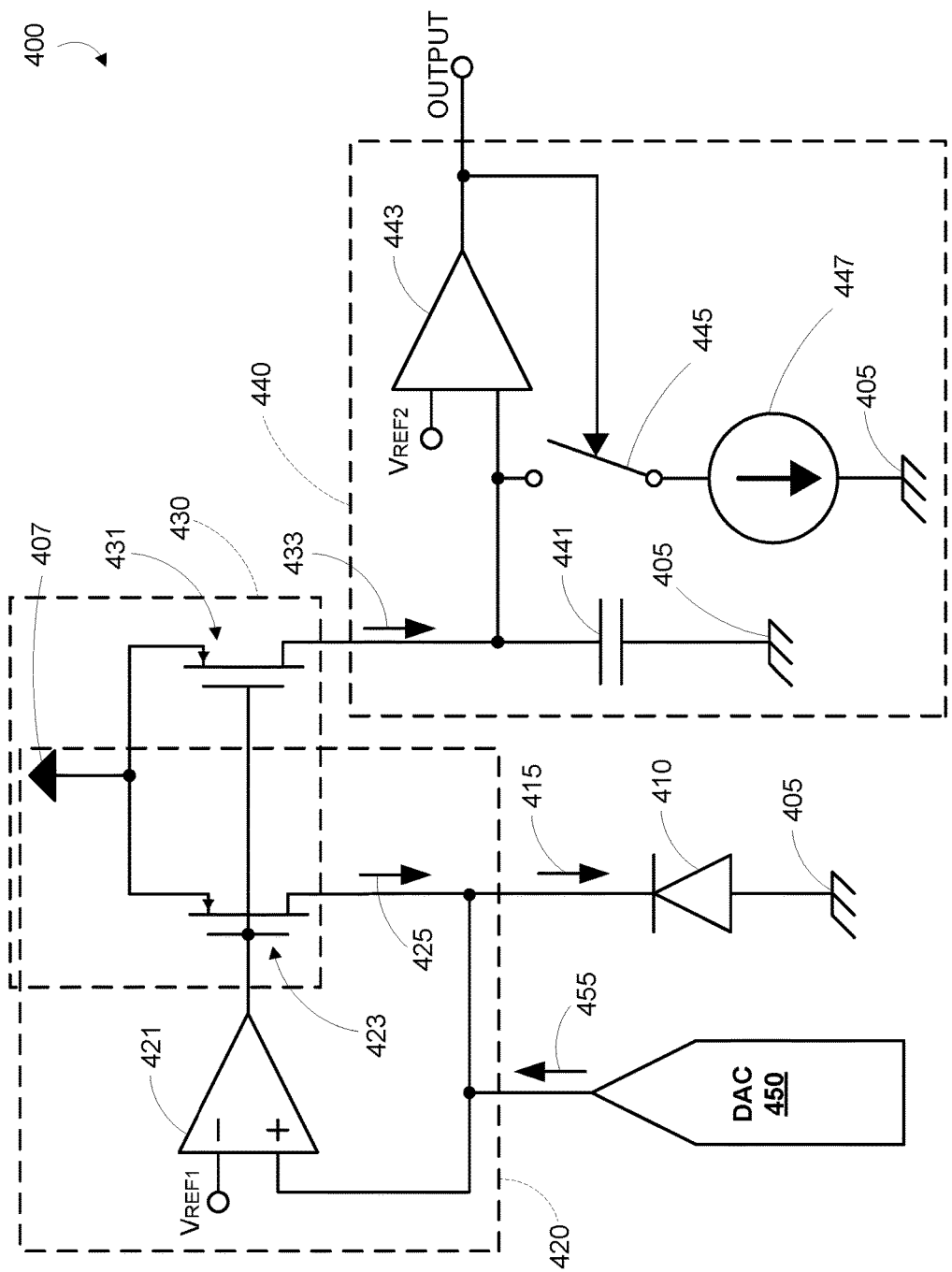
FIG. 4 illustrates an example circuit for generating a digital output related to light received from a portion of subsurface vasculature.

FIG. 4 is a circuit diagram of a photodiode 410 and example electronics 400 configured as described herein. The photodiode 410 is configured to receive light (e.g., visible light, infrared light, ultraviolet light) from an environment of interest (e.g., from a portion of subsurface vasculature of, e.g., a sclera, eyelid, or other element(s) of an eye) in response to illumination. The illumination could include illumination by ambient light (e.g., direct or indirect sunlight, light from a lamp or lighting fixture, light from a display, light from some other ambient light directed toward the environment of the environment of interest) and/or by light emitted by a light source in a body-mountable device of other device that includes the photodiode 410 and example electronics 400. The example electronics 400 includes a common electrical ground 405 and a voltage supply 407. Elements of the electronics 400 corresponding to electronic elements for operating photodiodes as described elsewhere herein are enclosed by dashed-line boxes. The electronics 400 include components corresponding to a photodiode voltage source 420, a current mirror 430, and a sigma-delta modulator 440. The electronics 400 additionally include a current-mode DAC 450 configured to provide a specified current 455 to the photodiode 410. The voltage supply 407 could be that same as a voltage supply used to power one or more other elements of the electronics 400 (e.g., operational amplifiers, DACs, comparators, current sinks of 420, 430, 440, 450) than the illustrated elements connected to the voltage supply 407 or could be a separate voltage supply.

The photodiode 410 could be configured in a variety of ways and include a variety of components/materials. The photodiode 410 could include silicon, germanium, indium gallium arsenide, lead(II) sulfide, or other materials, dopants, or combinations thereof according to an application. The materials and/or configuration of the photodiode 410 and/or associated components (e.g., filters, mirrors, diffraction gratings, Bragg reflectors/filters, lenses, or other optical elements) could be selected and/or configured such that the photodiode 410 has one or more specified properties. For example, the photodiode 410 and associated components could be configured such that a current 415 through the photodiode 410 when the photodiode voltage source 420 is applying a specified voltage to reverse-bias the photodiode 410 is related to one or more properties of light received by the photodiode 410. For example, an amplitude of the current 415 could be related to the intensity of the received light within a specified range of wavelengths, where the specified range of wavelengths is related to the composition and configuration (e.g., of filters and of the semiconductor(s) and dopant(s) used to create the photodiode 410, the area of a sensitive region of the photodiode 410). In some examples, such a specified range of wavelengths could be related to an absorption profile of blood, such that an absolute and/or relative volume of blood, an oxygen saturation of blood, or some other property of blood in a portion of subsurface vasculature could be related to the current 415. In some examples, one or more properties of a sensitive region of the photodiode 410 could be specified (e.g., a sensitive area of the photodiode 410 could measure approximately 700 microns by 700 microns). A dark current, a sensitivity of the current 415 to changes in amplitude or other properties of received light, or other properties of the photodiode 410 could be specified.

The photodiode voltage source 420 includes an operational amplifier 421 whose output is connected to the gate of a first field-effect transistor (FET) 423. The first FET 423 is connected to the voltage source 407, the photodiode 410, the DAC 450, and the non-inverting input of the operational amplifier 421 in a negative-feedback topology such the operational amplifier 421 generates outputs to the first FET 423 such that a voltage across the photodiode 410 is approximately equal to a first reference voltage $V_{REF1}$ applied to the inverting input of the operational amplifier 421. This includes the output of the operational amplifier 421 being such that a first FET current 425 flowing through the first FET 423 is equal to the photodiode current 415 reduced by an amount substantially equal to the DAC current 455.

Note that the components and connections thereof illustrated in FIG. 4 as part of the photodiode voltage source 420 are meant as non-limiting examples. Other components, circuit topologies, or other configurations of electronic components could be used to provide a photodiode voltage source configured to apply a voltage to the photodiode 410 such that the photodiode 410 is reverse-biased. When reverse biased in this way, the current through the photodiode 410 (e.g., 415) is related to the light received by the photodiode from an environment of interest (e.g., a portion of subsurface vasculature). For example, the first FET 423 could instead include one or more other types of transistors (e.g., bipolar junction transistors (BJTs), metal-oxide-semiconductor field effect transistors (MOSFETs), junction gate field effect transistors (JFETs)) or other electronic elements. Further, the photodiode voltage source 420 could include elements other than an operational amplifier (e.g., 421) configured in negative feedback or according to some other topology or scheme to apply a specified voltage to the photodiode 410. For example, the photodiode voltage source 420 could include one or more transistors configured to apply a specified voltage across the photodiode 410. Further, the specified voltage (e.g., $V_{REF1}$) could be the output of a resistive divider, an ADC, a voltage reference, or some other source of a specified voltage and could have a voltage value specified according to an application (e.g., specified such that the photodiode 410 has a specified level of current sensitivity to the intensity of received light).

The current mirror 430 is configured to present a current mirror output current 433 to the sigma-delta modulator 440 that is related to the photodiode current 415. Current divider 430 includes the first FET 423 (that is also part of the photodiode voltage source 420) and a second FET 431. The gate (i.e., the control terminal) of the second FET 431 is connected to the gate of the first FET 423 and to the output of the operational amplifier 421. The second FET 431 is additionally connected to the voltage source 407 and the sigma-delta modulator 440 such that the current mirror output current 433 is related to the first FET current 425 and thus to the photodiode current 415. Note that other types of transistor (e.g., BJTs, MOSFETs, JFETs) could be used instead of or in combination with the illustrated first and second FETs 423, 431. Further the configuration of a current mirror used to present a current to a sigma-delta modulator that is related to the current through a photodiode (e.g., 440 and 410, respectively) could include additional or alternate components configured in a similar or different topology from that shown here.

Note that a relationship between the current mirror output current 433 and the first FET current 425 could be related to the configuration of the current mirror 430. Specifically, a ratio between the current mirror output current 433 and the first FET current 425 (i.e., a transfer ratio of the current mirror 430) could be related to a ratio between properties and/or measurements of features of the corresponding first and second FETs 423, 431. For example, the transfer ratio of the current mirror 430 could be related to a ratio of the widths of the corresponding first and second FETs 423, 431. In some examples, such a ratio could be specified to one (i.e., a transfer ratio of unity) by specifying that the characteristics of the first and second FETs 423, 431 (e.g., channel width, temperature, gate properties, semiconductor properties) be substantially identical. This could be accomplished by forming the first and second FETs 423, 431 near to each other on the same semiconductor chip or wafer. Alternatively, the first and second FETs 423, 431 could be formed on the same wafer and having substantially the same configuration excepting one property (e.g., a channel width) that is different between the first and second FETs 423, 431 such that the transfer ratio of the current mirror 430 is some specified value other than unity. Other properties of other types of transistors used to form a current mirror (e.g., gate width of BJTs) could be similarly specified to achieve a current mirror having a specified transfer ratio.

The sigma-delta modulator 440 is configured to receive an input (e.g., current mirror output current) and to provide a digital output (OUTPUT) related to the input. As illustrated in FIG. 4, example sigma-delta modulator 440 includes a capacitor 441, a comparator 443, and a switched current sink comprising an electronic switch 445 and a current sink 447. The capacitor 441 is connected between the common electrical ground 405 and the input to the sigma-delta modulator 440 such that the capacitor 441 is charged by the input current (i.e., by 433). The comparator 443 is configured to compare the voltage across the capacitor 441 to a reference voltage $V_{REF2}$ and to generate a digital pulse when the voltage across the capacitor 441 is greater than $V_{REF2}$. The output of the comparator 443 is used as the OUTPUT of the sigma-delta modulator. The output of the comparator 443 is further used to operate the electronic switch 445 of the switched current sink such that each pulse output from the comparator 443 causes the current sink 447 to discharge a specified current from the capacitor 441 such that the capacitor 441 is discharged by a specified amount (e.g., by a specified amount of charge) for each digital pulse output by the comparator 443.

The comparator 443 could be clocked such that digital output pulses of the comparator are only generated at specified points in time relative to a clock signal provided to the comparator 443 (e.g., by a controller, a multivibrator, a quartz oscillator, or some other clock source). Parameters of operation of the sigma-delta modulator 440 (e.g., the voltage value of $V_{REF2}$, a clock frequency of a clock signal applied to the comparator 443, a width and/or duty cycle of digital pulses output by the comparator 443, a level of current sunk by the current sink 447) could be specified and/or changed such that the digital OUTPUT of the sigma-delta modulator 440 was related to the photodiode current 415 with a specified resolution, sample frequency, oversample frequency, or other property related to an application. For example, $V_{REF2}$ could be the output of an ADC or some other controllable voltage source and could be adjusted (e.g., lowered) to adjust a resolution (e.g., to increase a resolution) of the sigma-delta modulator. In another example, the current sunk by the current source 447 could be a specified value (e.g., 5 nanoamps) related to a resolution of the sigma-delta modulator 440, and could further be controllable (e.g., could be controlled between two or more specified values of sunk current) to control the resolution of the sigma-delta modulator 440.

In an example wherein the photodiode 410 is configured to receive light from a portion of subsurface vasculature and the digital output of the electronics 400 is used to determine a pulse rate of blood in the portion of subsurface vasculature. The configuration of the electronics 400 (e.g., a value of $V_{REF2}$, a current sunk by the current sink 447, a pulse width and/or clock frequency of the comparator 443) could be specified to allow determination of the frequency of the pulse rate within a specified accuracy using the digital output of the sigma-delta modulator 440. For example, an effective sample rate of the sigma-delta modulator 440 equal to or greater than 1 kilohertz in order to determine a pulse rate with greater than one beat-per-minute accuracy up to a pulse rate of 240 beats-per-minute.

In order to achieve a specified effective sample rate, a clock frequency applied to the comparator could be specified to be greater than the effective sample rate multiplied by a factor relating to a desired number of bits of resolution of the output relative to the input of the modulator 440. For example, an effective sample rate of 50 Hertz and a resolution of 12 bits could specify that the clock frequency applied to the sigma-delta modulator 440 be greater than 50*2^12=204800 Hertz. Further, parameters of operation of the electronics 400 (e.g., $V_{REF1}$, $V_{REF2}$, a transfer ratio of the current mirror 430, the value of current sunk by the current sink 447, a pulse width of pulses output by the comparator 443) could be specified relative to a current resolution of the photodiode current 412 specified according to an application. For example, the electronics 400 could be configured to generate a digital output that is related to the current through the photodiode 410 (i.e., 415) with a resolution that is less than approximately 100 picoamps.

Note that the configuration and connection of components of the sigma-delta modulator 440 as illustrated in FIG. 4 is meant as a non-limiting example. Additional or alternative components configured in a similar or different topology from that shown here are anticipated to provide a sigma-delta modulator configured to generate a digital output (e.g., OUTPUT) related to an input current (e.g., 433). Further a sigma-delta modulator (e.g., 440) could be configured to generate a digital output related to the current through multiple photodiodes (e.g., 410). For example, a plurality of photodiodes and corresponding plurality of respective capacitors, photodiode voltage sources, and current mirrors (configured similarly or differently to, e.g., 441, 420, 430, respectively) could be configured to input current to a single sigma-delta modulator (e.g., 440). In a particular example, a multiplexer or other electronic component could be interposed between components of the sigma-delta modulator and the plurality of photodiodes, photodiode voltage sources, current mirrors, capacitors, and/or other electronic components. The digital output of such a multiplexed sigma-delta modulator could thus correspond to a plurality of photodiode currents of the respective plurality of photodiodes according to a time division multiplexing scheme or according to some other relationship. In some embodiments, two or more photodiodes could be configured to received light from the same portion of subsurface vasculature having wavelengths within respective two or more ranges of wavelengths (e.g., ranges of wavelengths approximately equal to 700 nanometers and 900 nanometers, respectively) and the digital output, related to the lights received from the two or more photodiodes, could be used to determine an oxygen saturation or other information about blood in the portion of subsurface vasculature.

The DAC 450 could be configured in a variety of ways familiar to one skilled in the art. For example, the DAC 450 could include an R-2R ladder, a binary-weighted DAC, an amplifier, a pulse width modulator, a delta-sigma modulator, a successive-approximation DAC, or some other components or combination thereof configured to source and/or sink a specified controllable DAC current 455. In some examples, the DAC 450 could include an electronic switch connected in series with a resistor having a specified resistance. The series combination of the electronic switch and the resistor could be connected between the photodiode (as shown in FIG. 4) and the common electrical ground 405 or to some other specified voltage relative to the common electrical ground 405. The electronic switch could be operated according to a pulse width modulation scheme or according to some other scheme to source and/or sink a specified DAC current 455 to/from the photodiode 410. Instantaneous and/or mean values of current specified to control the DAC 450 to produce DAC current 455 could be determined in a variety of ways based on a variety of factors. In some examples, the DAC 450 could be operated to remove a low-frequency offset from the input (e.g., 433) received by the sigma-delta modulator by injecting a current (e.g., 455) related to the low-frequency offset into the photodiode 410.

The digital output (OUTPUT) of the electronics 400 could be used in a variety of ways according to an application. In some examples, the digital output could be decimated, e.g., specified time periods (e.g., a plurality of time periods having durations equal to a specified number of clock cycles) of the digital output could be used to generate respective digital output values by, e.g., summing the number of pulses in each of the time periods. In this way, a plurality of digital values related to the current through the photodiode 410 during a respective plurality of time periods could be determined. The digital output (OUTPUT) could be transmitted to some other system (e.g., a controller of a device including the electronics; to another system in communication with such a device); additionally or alternatively, a signal or value (e.g., a digital value determined through decimation of the OUTPUT) could be transmitted to some other system. A signal or value (e.g., a decimated digital value) based on the OUTPUT could be used to determine one or more properties of an environment that emitted the light received by the photodiode 410 (e.g., a volume or some other information about blood in a portion of subsurface vasculature). Additionally or alternatively, some other information (e.g., timing information) about the OUTPUT could be used to determine one or more properties of an environment that emitted the light received by the photodiode 410. For example, an autocorrelation, a spectrogram, a Fourier transform, or some other operation could be performed based on a sequence of digital pulses in OUTPUT and used to determine some information (e.g., a rate and/or phase of heart beats of a heart pumping blood through a portion of subsurface vasculature).

The electronics 400 could be configured to generate a digital output while consuming very little power. For example, photodiodes and related electronics disclosed herein could be included in a low-power environmental sensor that is part of a distributed sensor network, a low-power body-mountable (e.g., eye-mountable) device, or some other device having access to a limited power budget (e.g., having a low-capacity battery, being configured to scavenge power from environmental sources, being configured to be powered by received electromagnetic radiation from a reader or from some other source). In such examples, the electronics 400 and photodiode 410 could be configured to operate while using less than approximately 1 microamp, or preferentially less than approximately 500 nanoamps.

IV. Example Methods

Figure 5:
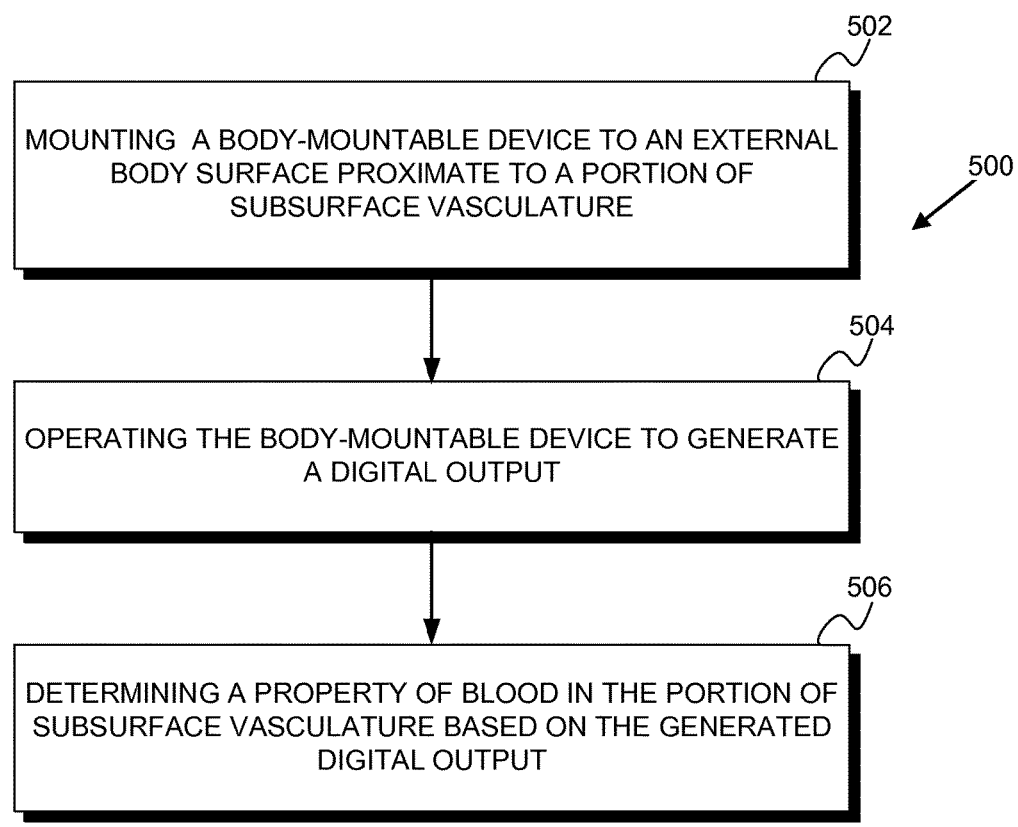
FIG. 5 is a flowchart of an example process for operating a light sensor in a body-mountable device to detect light received from a portion of subsurface vasculature.

FIG. 5 is a flowchart of a method 500 for operating a light sensor in a body-mountable device to measure light (e.g., visible light, infrared light, ultraviolet light) received from a portion of subsurface vasculature of a body (e.g., of a cornea, iris, sclera, eyelid, or other aspect of an eye of the body). The body-mountable device includes (i) a photodiode configured to detect the light received from the portion of subsurface vasculature, (ii) a photodiode voltage source configured to apply a voltage to the photodiode such that the photodiode is reverse biased and such that a current through the photodiode is related to the received light, (iii) a sigma-delta modulator configured to receive an input and to provide a digital output related to the input, and (iv) a current mirror configured to provide an output current related to the current through the photodiode and to present the output current as an input to the sigma-delta modulator. The light received by the photodiode is related to blood in the portion of subsurface vasculature (e.g., to a volume, extinction coefficient, flow rate, pulse rate, oxygen saturation, or some other property or properties of the blood). The body-mountable device and elements thereof could be configured and/or operated as described herein. Further, the body-mountable device could include additional components configured to provide some functionality. For example, the body-mountable device could include a controller configured to operate elements of the body-mountable device and/or to determine a property of the blood based on the digital output provide by the sigma-delta modulator, an antenna configured to received electromagnetic energy to power the body-mountable device and/or to indicate information (e.g., to indicate the digital output and/or some signal determined from such) wirelessly, an electrochemical sensor, an accelerometer, or some other components or combinations thereof.

The method 500 includes mounting the body-mountable device to an external body surface proximate to a portion of subsurface vasculature (502). In some examples, the body-mountable device could be formed to substantially conform to a cornea of an eye of the body, and the device could be mounted on the cornea such that the photodiode receives light from a portion of subsurface vasculature of the cornea, iris, sclera, eyelid, or other aspect of the eye. The body-mountable device could be mounted to the eye such that the photodiode receives light from a specified portion of subsurface vasculature and/or a portion of subsurface vasculature in a specified portion, aspect, or region of the eye (e.g., a region of the eye lateral to the pupil of the eye); that is the body-mountable device could be emplaced on the eye such that a location and/or orientation of the body-mountable device relative to the eye is specified. The body-mountable device could be configured such that motions, features, or other aspects or processes of the eye cause the body-mountable device to be aligned with (i.e., to have a specified location and/or orientation relative to) the eye; for example, the body-mountable device could be weighted, or could have a shape that interacted with elements of the eye (e.g., a flattened edge that is aligned by eyelid motion of the eye) such that the device is aligned.

The method 500 includes operating the body-mountable device to generate the digital output (504). This could include applying a voltage (i.e., applying power) to the electronics (e.g., photodiode voltage source, current mirror, and sigma-delta modulator, among other components). This could include setting one or more parameters or controls of the electronics (e.g., set or reference voltages, clock frequencies, current sink values) such that the digital output has one or more specified properties (e.g., an effective sample rate, a resolution) relative to the current through the photodiode and/or to one or more properties of the light received from the portion of subsurface vasculature. Operating the body-mountable device to generate the digital output (504) could include any process or operation as described herein for operating electronics (e.g., 400, other electronics herein) to generate a digital output that is related to light received by the photodiode. Operating the body-mountable device to generate the digital output (504) could include operating elements (e.g., light-emitting diode(s) (LED(s))) of the body-mountable device to generate a light (e.g., a visible light, an infrared light, an ultraviolet light, light having a specified spectral profile) to illuminate the portion of subsurface vasculature. Additionally or alternatively, light received by the photodiode from the portion of subsurface vasculature could be received in response to illumination of the portion of subsurface vasculature by ambient light sources.

The method 500 further includes determining a property of blood in the portion of subsurface vasculature based on the generated digital output (506). In some examples, this could include a controller or other processor of the body-mountable device performing the determination; additionally or alternatively, the body-mountable device could indicate a signal (e.g., using an antenna of the body-mountable device) related to the digital output (e.g., the digital output, a decimated version thereof, some other signal based on the digital output), and some other system (e.g., a reader configured to wirelessly communicate with and/or power the body-mountable device) could receive the indicated signal and determine a property of blood in the portion of subsurface vasculature based on the received signal. Determined properties of the blood could include a blood volume, a blood flow rate, a pulse rate, an extinction or absorption coefficient, an oxygen saturation, or some other property of the blood.

The method 500 could include additional steps or elements in addition to those depicted in FIG. 5 (i.e., 502, 504, 506). For example, the method 500 could include detecting light received from the portion of subsurface vasculature at a plurality of points in time and determined a property of blood (e.g., a property of blood flow) in the portion of subsurface vasculature based on the plurality of detected received lights. For example, an intensity of the received light could be detected at a plurality of points in time and used to determine a respective plurality of volumes of blood in the portion of subsurface vasculature. A blood flow, a pulse rate, a blood flow profile, or some other information about the blood in the portion of subsurface vasculature could be determined based on the plurality of detected received lights and/or the plurality of determined blood volumes. In another example, the photodiode could be configured to receive light within a first range of wavelengths and the body-mountable device could include further photodetector configured to detect light form the portion of subsurface vasculature in a second range of wavelengths. The method 500 could include operating the further photodetector to detect the light in the second range of wavelengths and determining an oxygen saturation of blood in the portion of subsurface vasculature based on the detected received lights in the first and second ranges of wavelengths (e.g., based on a ratio of the intensities of the lights and absorption spectra of oxygenated and deoxygenated blood within the first and second ranges, or according to some other relationship operation). Other additional elements of the method 500 are anticipated.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A body-mountable device comprising:
   a photodiode, wherein the photodiode is positioned to detect light received from a portion of subsurface vasculature, wherein the light received from the portion of subsurface vasculature is related to blood in the portion of subsurface vasculature;
   a photodiode voltage source, wherein the photodiode voltage source applies a voltage to the photodiode such that the photodiode is reverse biased, wherein a photodiode current through the photodiode is related to the light received from the portion of sub surface vasculature;
   a current-mode digital-to-analog converter (DAC), wherein the current-mode DAC sources or sinks a DAC current;
   a current mirror, wherein the current mirror has an input current path and an output current path, wherein the current mirror provides an output current in the output current path that is related to an input current in the input current path, wherein the photodiode and current-mode DAC are connected in parallel to the input current path of the current mirror such that the input current is related to the photodiode current and DAC current; and
   a sigma-delta modulator coupled to the output current path of the current mirror, wherein the sigma-delta modulator provides a digital output related to the output current in the output current path of the current mirror.

2. The body-mountable device of claim 1, wherein the body-mountable device further comprises:
   a shaped polymeric material, wherein the shaped polymeric material has a concave surface and a convex surface, wherein the concave surface can be removably mounted on an eye and the convex surface is opposite the concave surface;
   a substrate at least partially embedded within the shaped polymeric material, wherein the photodiode, photodiode voltage source, and sigma-delta modulator are disposed on the substrate;
   an antenna disposed on the substrate, wherein the antenna is operable to indicate a signal related to the digital output of the sigma-delta modulator.

3. The body-mountable device of claim 2, wherein the photodiode is directed toward the concave surface of the shaped polymeric material such that the portion of subsurface vasculature is a portion of vasculature of the eye when the concave surface is mounted on the eye.

4. The body-mountable device of claim 3, wherein the photodiode is disposed on the substrate such that the portion of subsurface vasculature is a portion of subsurface vasculature that is disposed in a lateral region of the eye relative to a pupil of the eye when the concave surface is mounted on the eye.

5. The body-mountable device of claim 2, wherein the photodiode is directed toward the convex surface of the shaped polymeric material such that the portion of subsurface vasculature is a portion of vasculature of an eyelid of the eye when the concave surface is mounted on the eye and the eyelid is at least partially closed over the eye.

6. The body-mountable device of claim 1, wherein the photodiode current through the photodiode is related to an intensity of the light received from the portion of subsurface vasculature, and wherein the intensity of the light is related to a volume of the blood in the subsurface vasculature.

7. The body-mountable device of claim 1, wherein the current mirror comprises a first transistor and a second transistor, wherein the first transistor is a part of the photodiode voltage source and is electronically connected between a voltage source and the photodiode, wherein the photodiode voltage source is configured to operate the first transistor by applying a control signal to a control terminal of the first transistor such that a voltage across the photodiode is substantially equal to a specified voltage, wherein the second transistor is electronically connected between the voltage source and the sigma-delta modulator, and wherein the control signal is additionally applied to a control terminal of the second transistor.

8. The body-mountable device of claim 1, wherein the sigma-delta modulator comprises:
   a capacitor, wherein the capacitor is coupled to the output current path of the current mirror;
   a switched current sink, wherein the switched current sink can be operated to discharge a specified current from the capacitor; and
   a comparator, wherein the comparator compares a voltage across the capacitor to a specified reference voltage, wherein the comparator generates a digital pulse when the voltage across the capacitor is greater than the specified reference voltage, and wherein the switched current sink is operated by the digital pulses generated by the comparator such that the switched current sink discharges the capacitor by a specified amount for each generated digital pulse.

9. The body-mountable device of claim 1, wherein the digital output of the sigma-delta modulator is related to the photodiode current through the photodiode with a resolution that is less than approximately 100 picoamps.

10. The body-mountable device of claim 1, further comprising an antenna, wherein the antenna is operable to receive radio frequency energy to power the body-mountable device.

11. The body-mountable device of claim 1, further comprising an antenna, wherein the antenna is operable to wirelessly indicate a signal related to the digital output of the sigma-delta modulator.

12. The body-mountable device of claim 1, wherein the photodiode current through the photodiode is related to an intensity of the light received from the portion of subsurface vasculature within a first range of wavelengths, wherein the body-mountable device further includes a photodetector that can detect an intensity of light received from the portion of subsurface vasculature within a second range of wavelengths, and wherein the intensity of the light detected by the photodiode and the intensity of the light detected by the photodetector are related to an oxygen saturation of blood in the portion of sub surface vasculature.

13. A method, comprising:
  receiving, by a photodiode in a body-mountable device, light from a portion of subsurface vasculature, wherein the light received from the portion of subsurface vasculature is related to blood in the portion of subsurface vasculature;
  applying, by a photodiode voltage source in the body-mountable device, a voltage to the photodiode such that the photodiode is reverse biased, wherein a photodiode current through the photodiode is related to the light received from the portion of subsurface vasculature;
  providing, by a current-mode digital-to-analog converter (DAC) in the body-mountable device, a DAC current;
  providing, by a current mirror in the body-mountable device, an output current in an output current path of the current mirror, wherein the output current is related to an input current in an input current path of the current mirror, and wherein the photodiode and current-mode DAC are connected in parallel to the input current path of the current mirror such that the input current is related to the photodiode current and DAC current; and
  generating, by a sigma-delta modulator in the body-mountable device, a digital output related to the output current in the output current path of the current mirror.

14. The method of claim 13, further comprising:
  determining a property of blood in the portion of subsurface vasculature based on the generated digital output.

15. The method of claim 14, wherein the photodiode current through the photodiode is related to an intensity of the light received from the portion of subsurface vasculature within a first range of wavelengths, wherein the body-mountable device further includes a photodetector that can detect an intensity of light received from the portion of subsurface vasculature within a second range of wavelengths, wherein the method further includes operating the photodetector to detect the intensity of light received from the portion of subsurface vasculature within the second range of wavelengths, and wherein determining the property of blood in the portion of subsurface vasculature based on the generated digital output comprises determining an oxygen saturation of blood in the portion of subsurface vasculature based on the generated digital output and the intensity of light detected using the photodetector.

16. The method of claim 14, wherein the photodiode current through the photodiode is related to an intensity of light received from the portion of subsurface vasculature, wherein the intensity of the light received from the portion of subsurface vasculature is related to a volume of the blood in the subsurface vasculature, wherein determining the property of blood in the portion of subsurface vasculature comprises determining the volume of blood in the portion of subsurface vasculature based on the digital output generated by the sigma-delta modulator, wherein determining the property of blood in the portion of subsurface vasculature based on the generated digital output is performed a plurality of times at a plurality of respective points in time to generate a plurality of respective determined volumes of blood in the portion of subsurface vasculature, and further comprising:
  determining a property of blood flow in the portion of subsurface vasculature based on the plurality of determined volumes of blood in the portion of subsurface vasculature.

17. The method of claim 13, wherein the body-mountable device further comprises: (i) a shaped polymeric material, wherein the shaped polymeric material has a concave surface and a convex surface, wherein the concave surface can be removably mounted on an eye and the convex surface is opposite the concave surface, and (ii) a substrate at least partially embedded within the shaped polymeric material, wherein the photodiode, photodiode voltage source, current-mode DAC, current mirror, and sigma-delta modulator are disposed on the substrate.

18. The method of claim 13, wherein the body-mountable device further comprises an antenna, and further comprising:
  indicating, using the antenna, a wireless signal related to the digital output of the sigma-delta modulator.

19. The method of claim 18, wherein the indicating comprises reflecting a radio-frequency signal received by the antenna.

20. The method of claim 13, wherein the body-mountable device further comprises an antenna, further comprising:
  using a radio-frequency signal received by the antenna to power the body-mountable device.

* * * * *